United States Patent
Gayer et al.

(10) Patent No.: US 6,730,799 B2
(45) Date of Patent: May 4, 2004

(54) PROCESS FOR PREPARING 3-(1-HYDROXYPHENYL-1-ALKOXIMINOMETHYL)DIOXAZINES

(75) Inventors: Herbert Gayer, Monheim (DE); Bernd Gallenkamp, Wuppertal (DE); Peter Gerdes, Aachen (DE); Ulrich Heinemann, Leichlingen (DE); Bernd-Wieland Krüger, Bergisch Gladbach (DE); Reinhard Lantzsch, Wuppertal (DE); Thomas Seitz, Langenfeld (DE); Uwe Stelzer, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/162,947

(22) Filed: Jun. 5, 2002

(65) Prior Publication Data

US 2002/0169316 A1 Nov. 14, 2002

Related U.S. Application Data

(62) Division of application No. 09/619,141, filed on Jul. 19, 2000, now Pat. No. 6,479,675, which is a division of application No. 09/180,251, filed as application No. PCT/EP97/02526 on May 16, 1997, now Pat. No. 6,150,521.

(30) Foreign Application Priority Data

| May 30, 1996 | (DE) | 196 21 696 |
| Dec. 9, 1996 | (DE) | 196 51 034 |
| Feb. 19, 1997 | (DE) | 197 06 399 |

(51) Int. Cl.⁷ ............ C07D 307/77; C07D 273/01; C07D 307/78
(52) U.S. Cl. ............ 549/467; 549/469; 544/65
(58) Field of Search ............ 544/65; 549/467, 549/469

(56) References Cited

U.S. PATENT DOCUMENTS 5,679,676 A   10/1997   Krüger et al. ............ 514/229.2

FOREIGN PATENT DOCUMENTS

| DE | 44 08 005 | 2/1995 |
| DE | 19744705 | 4/1999 |
| EP | 846 691 | 6/1998 |
| HU | 216 830 B | 9/1999 |
| HU | 216830 | * 9/1999 |
| WO | WO 99 19316 | 4/1999 |

OTHER PUBLICATIONS

Proc. Indian Acad. Sci., Sect. A, vol. 83A, No. 6, 1976, pp. 238–242, K.V. Rao, et al.; "Reactivity of—2–oximinocoumaranones".

Indian Journal of Chemistry, vol. 11, No. 10, 1973, pp. 989–990, O.P. Jha, "Synthesis of Abutic . . . Acid".

Tetrahedron Letters, No. 24, 1979, pp. 2221–2224, W.V. Curran, et al. "A Novel Conversion . . . 2–oxime".

Eur. J. Med. Chem.—Chim. Ther., vol. 19, No. 6, 1984, S. Smati, et al., "Syntheses et . . . alcanoiques".

Archive Der Pharmazie, vol. 306, No. 2, 1973, pp. 122–126, H. Loth et al., "Eine neue . . . cumaranonen".

Rao et al. Indian Journal of Chemistry, vol. 15B, paes 236–237 (1977).

Becket et al., Tetrahedron Letters, No. 9, pp. 719–720 (1976).

Stoermer et al., Chem. Berichte, vol. 35, paes 1640–1647 (1902).

Stoermer, Chem. Berichte, vol. 42, pp. 199–202 (1909).

Newkome et al., Journal of Organic Chemistry, vol. 50, pp. 4238–4245 (1985).

Henry, Chem. Berichte, vol. 7, p. 70 (1874).

* cited by examiner

*Primary Examiner*—Richard L. Raymond
*Assistant Examiner*—Sudhaker B. Patel
(74) *Attorney, Agent, or Firm*—Norris McLaughlin & Marcus

(57) ABSTRACT

The present invention relates to a plurality of novel processes and novel intermediates for preparing 3-(1-hydroxyphenyl-1-alkoximinomethyl)dioxazines, which are known as intermediates for preparing compounds having fungicidal properties (WO 95-04728).

6 Claims, No Drawings

PROCESS FOR PREPARING 3-(1-HYDROXYPHENYL-1-ALKOXIMINOMETHYL)DIOXAZINES

This application is a division of U.S. Ser. No. 09/619,141, filed on Jul. 19, 2000, now U.S. Pat. No. 6,479,675, which is a division of U.S. Ser. No. 09/180,251, filed on Nov. 6, 1998, now U.S. Pat. No. 6,150,521, which is a 371 of PCT/EP97/02526, filed on May 16, 1997, which claims priority under 35 USC 119 on the basis of German Application Nos. 196 21 696.6, filed on May 30, 1996; No. 196 51 034.1, filed on Dec. 9, 1996; and No. 197 06 399.3, filed Feb. 19, 1997.

The present invention relates to a plurality of novel processes and novel intermediates for preparing 3-(1-hydroxyphenyl-1-alkoximinomethyl)dioxazines, which are known as intermediates for preparing compounds having fungicidal properties (WO 95-04728).

It has already been disclosed that certain 3-(1-hydroxyphenyl-1-alkoximino-methyl)dioxazines can be prepared starting from the corresponding hydroxyphenyl-acetates (cf. WO 95-04728). Thus, for example (5,6-dihydro-1,4,2-dioxazin-3-yl)-(2-hydroxy-phenyl)-methanone O-methyl-oxime (1) is obtained by reacting methyl hydroxyphenylacetate (a) with dihydropyran, converting the dihydropyranyl ether (b) obtained in this way with t-butyl nitrite into methyl 2-[2-(tetrahydropyran-2-yloxy)-phenyl]-2-hydroximino-acetate (c), alkylating this compound with iodomethane to give methyl 2-[2-(tetrahydropyran-2-yloxy)-phenyl]-2-methoximino-acetate (d), reacting this with hydroxylamine to give 2-[2-(tetrahydropyran-2-yloxy)-phenyl]-2-methoximino-N-hydroxyacetamide (e), cyclizing the latter with dibromoethane to 3-{1-[2-(tetrahydropyran-2-yloxy)-phenyl]-1-methoximino-methyl}-5,6-dihydro-1,2,4-dioxazine (f), and finally removing the tetrahydropyranyl group using acid catalysis. This synthesis can be illustrated by the following scheme:

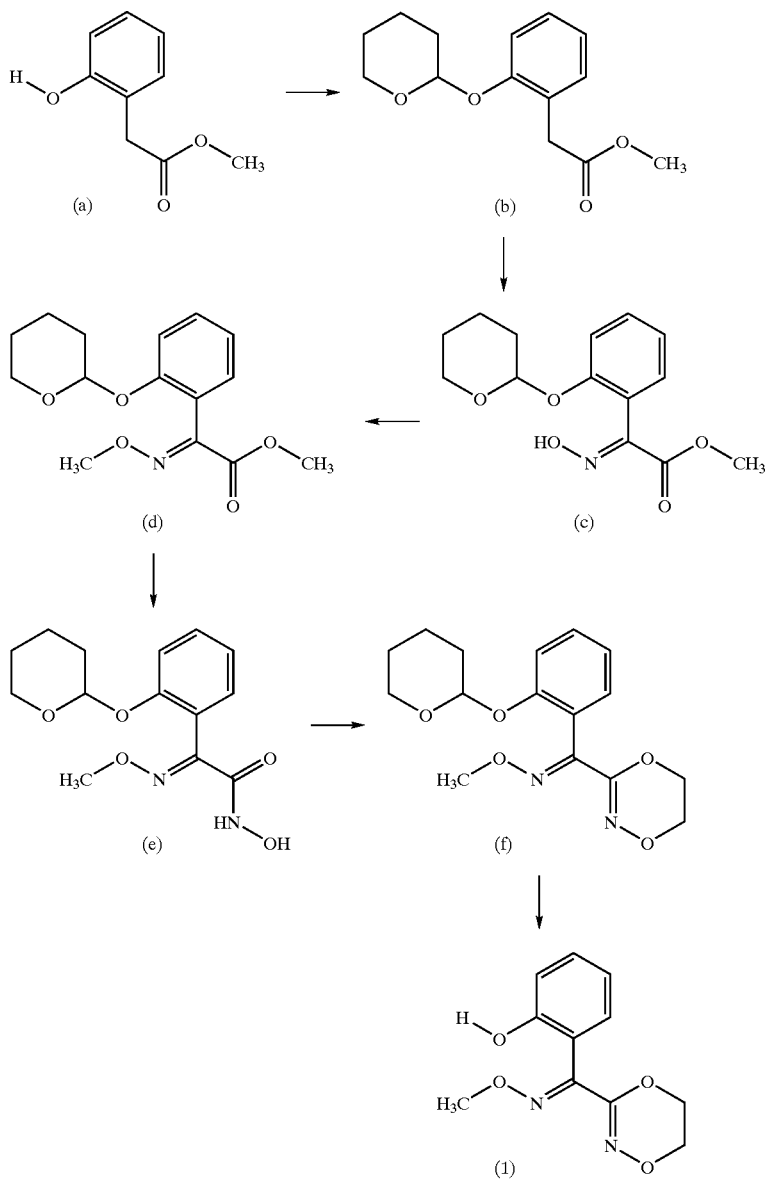

A major disadvantage of this process is the fact that it requires a large number of steps, some of which are of low yield, which significantly affects the profitability of this process.

It has now been found that 3-(1-hydroxyphenyl-1-alkoximinomethyl)dioxazines of the general formula

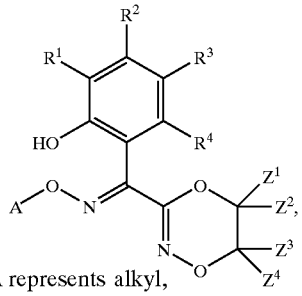
(I)

A represents alkyl, in which $R^2$, $R^3$ and $R^4$ are identical or different and each represent independently of one another hydrogen, halogen, cyano, nitro, respectively optionally halogen-substituted alkyl, alkoxy, alkylthio, alkylsulphinyl or alkylsulphonyl, and $Z^1$, $Z^2$, $Z^3$ and $Z^4$ are identical or different and each represent independently of one another hydrogen, alkyl, halogenoalkyl or hydroxyalkyl, or $Z^1$ and $Z^2$ or $Z^1$ and $Z^3$ or $Z^3$ and $Z^4$ form together with the respective carbon atoms that they are attached to a cycloaliphatic ring, are obtained when a) O-hydroxyethyl-O'-methyl-benzofurandione dioximes of the formula

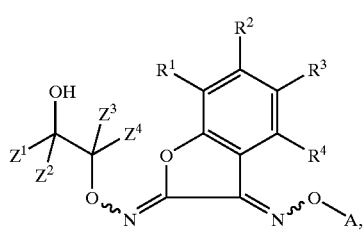
(II)

in which

A $R^1$, $R^2$, $R^3$, $R^4$, $Z^1$, $Z^2$ $Z^3$ and $Z^4$ are each as defined above, are rearranged, if appropriate in the presence of a diluent and, if appropriate, in the presence of an acid or a base, or b) hydroxybenzoyldioxazines of the formula

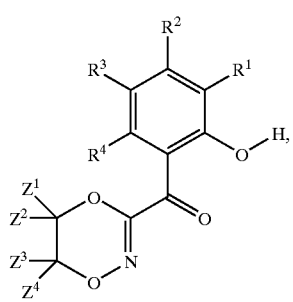
(III)

in which $R^1$, $R^2$, $R^3$, $R^4$, $Z^1$, $Z^2$, $Z^3$ and $Z^4$ are each as defined above, are reacted with an alkoxyamine of the formula

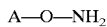
A—O—NH$_2$ (IV)

in which

A is as defined above or an acid addition complex thereof if appropriate in the presence of a diluent and, if appropriate, in the presence of an acid acceptor, or c) hydroxyphenyl-hydroximinomethyl-dioxazines of the formula

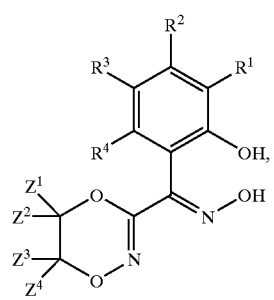
(V)

in which $R^1$, $R^2$, $R^3$, $R^4$, $Z^1$, $Z^2$, $Z^3$, and $Z^4$ are each as defined above, are reacted with an alkylating agent of the formula

A—X (VI)

in which

A is as defined above, and

X represents halogen, alkylsulphonyloxy, alkoxysulphonyloxy or arylsulphonyloxy, if appropriate in the presence of a diluent and, if appropriate, in the presence of a base.

In the definitions, the saturated or unsaturated hydrocarbon chains, such as alkyl, also in connection with hetero atoms, such as in alkoxy or alkylthio, are in each case straight-chain or branched.

The methods of the processes a-c) according to the invention are preferably. employed for preparing compounds of the formula (I) in which A represents methyl, ethyl, n- or i-propyl, $R^1$, $R^2$, $R^3$ and $R^4$ are identical or different and each represent independently of one another hydrogen, halogen, cyano or nitro, or represent alkyl, alkoxy, alkylthio, alkylsulphinyl or alkylsulphonyl, each of which is optionally substituted by 1 to halogen atoms and each of which has 1 to 6 carbon atoms, $Z^1$, $Z^2$, $Z^3$ and $Z^4$ are identical or different and each represent independently of one another hydrogen, alkyl or hydroxyalkyl having 1 to 4 carbon atoms or halogenoalkyl having 1 to 4 carbon atoms and 1 to 5 identical or different halogen atoms, or $Z^1$ and $Z^2$ or $Z^1$ and $Z^3$ or $Z^3$ and $Z^4$ form together with the respective carbon atoms that they are attached to a cycloaliphatic ring having five, six or seven carbon atoms.

Particular preference is given to preparing compounds of the formula (I) in which A represents methyl or ethyl, $R^1$, $R^2$, $R^3$ and $R^4$ are identical or different and each represent independently of one another hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, and $Z^1$, $Z^2$, $Z^3$ and $Z^4$ are identical or different and each represent independently of one another hydrogen, methyl, ethyl, n- or i-propyl, n-, i-, s- or t-butyl, hydroxymethyl, trifluoromethyl or trifluoroethyl, or $Z^1$ and $Z^2$ or $Z^1$ and $Z^3$ or $Z^3$ and $Z^4$ form together with the respective carbon atoms that they are attached to a cycloaliphatic ring having five, six or seven carbon atoms.

The O-hydroxyethyl-O'-methyl-benzofurandione dioximes required as starting materials in the practice of the process a) according to the invention are defined in a general way by the formula (II). In this formula (II), A, $R^1$, $R^2$, $R^3$, $R^4$, $Z^1$, $Z^2$, $Z^3$ and $Z^4$ preferably or particularly have those meanings already mentioned in connection with the description of the compounds of the formula (I) which can be prepared according to the invention as being preferred or particularly preferred for A, $R^1$, $R^2$, $R^3$, $R^4$, $Z^1$, $Z^2$, $Z^3$ and $Z^4$.

The starting materials of the formula (II) have not been disclosed before, and as novel compounds they also form part of the subject matter of the present application.

The O-hydroxyethyl-O'-methyl-benzofurandione dioximes of the formula (II) are obtained when process d) O-hydroxyethyl-benzofurandione monooximes of the formula (VII)

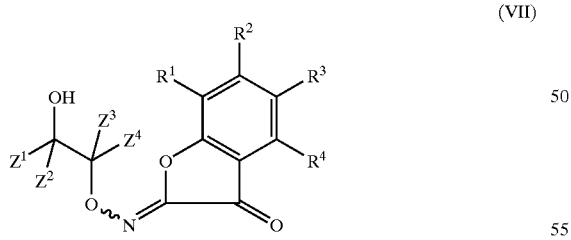

in which $R^1$, $R^2$, $R^3$, $R^4$, $Z^1$, $Z^2$, $Z^3$ and $Z^4$ are each as defined above are reacted with an alkoxyamine of the formula (IV) or an acid addition complex thereof if appropriate in the presence of a diluent and, if appropriate, in the presence of an acid acceptor, or process e) O-alkyl-benzofurandione dioximes of the formula (VIII)

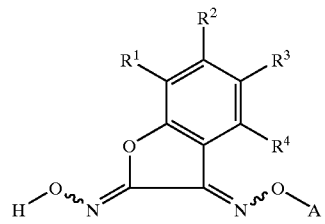

in which

A, $R^1$, $R^2$, $R^3$ and $R^4$ are each as defined above are reacted with an ethane derivative of the formula (IX)

in which $Y^1$ represents halogen, alkylsulphonyloxy, arylsulphonyloxy or alkanoyloxy, and G represents hydrogen, or $Y^1$ and G are linked to each other by a single bond, where $Y^1$ represents oxygen and G represents 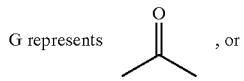, or $Y^1$ and G together represent a single bond, and $Z^1$, $Z^2$, $Z^3$ and $Z^4$ are each as defined above, if appropriate in the presence of a diluent and, if appropriate, in the presence of a base, or process f) O-hydroxyethyl-benzofurandione dioximes of the formula (X)

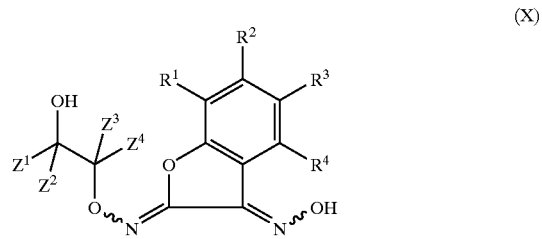

in which $R^1$, $R^2$, $R^3$, $R^4$, $Z^1$, $Z^2$, $Z^3$ and $Z^4$ are each as defined above are reacted with an alkylating agent of the formula (VI), if appropriate in the presence of a diluent and, if appropriate, in the presence of a base, or process m) O-oxyethyl-O'-methyl-benzofurandione dioximes of the formula

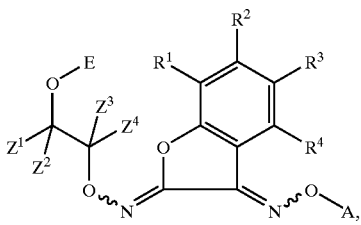

(XIII)

in which

A, $R^1$, $R^2$, $R^3$, $R^4$, $Z^1$, $Z^2$, $Z^3$ and $Z^4$ are each as defined above and E represents an acyl group or a ketal protecting group, are reacted with water or an alcohol, if appropriate in the presence of a diluent and, if appropriate, in the presence of an acid or a base.

The O-hydroxyethyl-benzofurandione monooximes required as starting materials in the practice of the process d) according to the invention are defined in a general way by the formula (VII). In this formula (VII), $R^1$, $R^2$, $R^3$, $R^4$, $Z^1$, $Z^2$, $Z^3$ and $Z^4$ preferably or particularly have those meanings already mentioned in connection with the description of the compounds of the formula (I) which can be prepared according to the invention as being preferred or particularly preferred for $R^1$, $R^2$, $R^3$, $R^4$, $Z^1$, $Z^2$, $Z^3$ and $Z^4$.

The starting materials of the formula (VII) have not been disclosed before, and as novel compounds they also form part of the subject matter of the present application.

The O-hydroxyethyl-benzofurandione monooximes of the formula (VII) are obtained when process g) benzofurandione monooximes of the formula

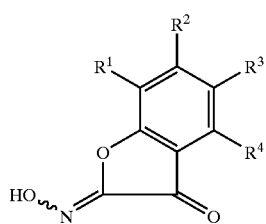

(XI)

in which $R^1$, $R^2$, $R^3$ and $R^4$ are each as defined above are reacted with an ethane derivative of the formula (IX), if appropriate in the presence of a diluent and, if appropriate, in the presence of a base, or process n) O-oxyethyl-benzofurandione monooximes of the formula

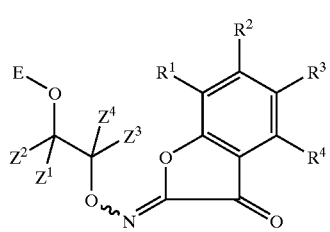

(XIV)

in which

E, $R^1$, $R^2$, $R^3$, $R^4$, $Z^1$, $Z^2$, $Z^3$ and $Z^4$ are each as defined above are reacted with water or an alcohol, if appropriate in the presence of a diluent and, if appropriate, in the presence of an acid or a base.

The benzofurandione monooximes required as starting materials in the practice of the process g) according to the invention are defined in a general way by the formula (XI). In this formula (XI), $R^1$, $R^2$, $R^3$ and $R^4$ preferably or particularly have those meanings already mentioned in connection with the description of the compounds of the formula (I) which can be prepared according to the invention as being preferred or particularly preferred for $R^1$, $R^2$, $R^3$ and $R^4$.

The benzofurandione monooximes of the formula (XI) are known and can be prepared by known methods (cf. Beilstein, E (II) 17, 462; Mameli, G. 56, 768; Chem. Ber. 35 (1902), 1640–1646; Proc. Indian Acad. Sci. Sect. A (1976) 83A(6), 238–242)).

The O-oxyethyl-benzofurandione monooximes required as starting materials in the practice of the process n) according to the invention are defined in a general way by the formula (XIV). In this formula (XIV), $R^1$, $R^2$, $R^3$, $R^4$, $Z^1$, $Z^2$, $Z^3$ and $Z^4$ preferably or particularly have those meanings already mentioned in connection with the description of the compounds of the formula (I) which can be prepared according to the invention as being preferred or particularly preferred for $R^1$, $R^2$, $R^3$, $R^4$, $Z^1$, $Z^2$, $Z^3$ and $Z^4$. E preferably or particularly has that meaning mentioned below in connection with the description of the compounds of the formula (XIII) according to the invention as being preferred or particularly preferred for E.

The starting materials of the formula (XIV) have not been disclosed before, and as novel compounds they also form part of the subject matter of the present application.

The O-oxyethyl-benzofurandione monooximes of the formula (XIV) are obtained when process o) benzofurandione monooximes of the formula (XI) are reacted with an ethanol derivative of the formula

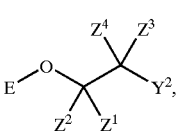

(XV)

in which

E, $Z^1$, $Z^2$, $Z^3$ and $Z^4$ are each as defined above, and $Y^2$ represents halogen, alkylsulphonyloxy, arylsulphonyloxy or alkanoyloxy, if appropriate in the presence of a diluent and, if appropriate. in the presence of an acid acceptor.

The benzofurandione monooximes of the formula (XI) required as starting materials in the practice of the process o) according to the invention have already been described in the description of the process g) according to the invention.

The O-alkyl-benzofurandione dioximes required as starting materials in the practice of the process e) according to the invention are defined in a general way by the formula (VIII). In this formula (VIII), $R^1$, $R^2$, $R^3$ and $R^4$ preferably or particularly have those meanings already mentioned in connection with the description of the compounds of the formula (I) which can be prepared according to the invention as being preferred or particularly preferred for $R^1$, $R^2$, $R^3$ and $R^4$.

The starting materials of the formula (VIII) have not been disclosed before, and as novel compounds they also form part of the subject matter of the present application.

The O-hydroxyethyl-benzofurandione monooximes of the formula (VIII) are obtained when process h) benzofurandione monooximes of the formula (XI) are reacted with an alkoxyamine of the formula (IV), if appropriate in the presence of a diluent and, if appropriate, in the presence of an acid acceptor, or process p) benzofurandione dioximes of the formula (XII)

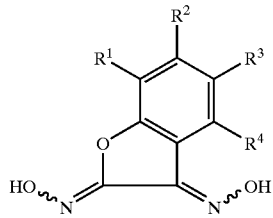

in which $R^1$, $R^2$, $R^3$ and $R^4$ are each as defined above are reacted with an alkylating agent of the formula (VI), if appropriate in the presence of a diluent and, if appropriate, in the presence of a base.

The benzofurandione monooximes of the formula (XI) required as starting materials in the practice of the process h) according to the invention have already been described in the description of the process g) according to the invention.

The benzofurandione dioximes required as starting materials in the practice of the process p) according to the invention are defined in a general way by the formula (XII). In this formula (XII), $R^1$, $R^2$, $R^3$ and $R^4$ preferably or particularly have those meanings already mentioned in connection with the description of the compounds of the formula (I) which can be prepared according to the invention as being preferred or particularly preferred for $R^1$, $R^2$, $R^3$ and $R^4$.

The benzofurandione dioximes of the formula (XII) are known and can be prepared by known methods (cf. Chem. Ber. 42 (1909), 202).

The O-hydroxyethyl-benzofurandione dioximes required as starting materials in the practice of the process f) according to the invention are defined in a general way by the formula (X). In this formula (X), $R^1$, $R^2$, $R^3$ and $R^4$ preferably or particularly have those meanings already mentioned in connection with the description of the compounds of the formula (I) which can be prepared according to the invention as being preferred or particularly preferred for $R^1$, $R^2$, $R^3$ and $R^4$.

The starting materials of the formula (X) have not been disclosed before, and as novel compounds they also form part of the subject matter of the present application.

The O-hydroxyethyl-benzofurandione dioximes of the formula (X) are obtained when process i) O-hydroxyethyl-benzofurandione monooximes of the formula (VII)

are reacted with hydroxylamine—or an acid addition complex thereof— if appropriate in the presence of a diluent and, if appropriate, in the presence of an acid acceptor, or process q) O-oxyethyl-benzofurandione dioximes of the formula (XVI)

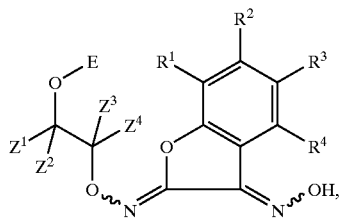

in which

E, $R^1$, $R^2$, $R^3$, $R^4$, $Z^1$, $Z^2$, $Z^3$ and $Z^4$ are each as defined above, are reacted with water or an alcohol, if appropriate in the presence of a diluent and, if appropriate, in the presence of an acid or a base.

The O-hydroxyethyl-benzofurandione monooximes of the formula (VII) required as starting materials in the practice of the process i) according to the invention have already been described in the description of the process d) according to the invention.

The O-oxyethyl-benzofurandione dioximes required as starting materials in the practice of the process q) according to the invention are defined in a general way by the formula (XVI). In this formula (XVI), $R^1$, $R^2$, $R^3$, $R^4$, $Z^1$, $Z^2$, $Z^3$ and $Z^4$ preferably or particularly have those meanings already mentioned in connection with the description of the compounds of the formula (I) which can be prepared according to the invention as being preferred or particularly preferred for $R^1$, $R^2$, $R^3$, $R^4$, $Z^1$, $Z^2$, $Z^3$ and $Z^4$. E preferably or particularly has those meanings mentioned below in connection with the description of the compounds of the formula (XIII) according to the invention as being preferred or particularly preferred for E.

The starting materials of the formula (XVI) have not been disclosed before, and as novel compounds they also form part of the subject matter of the present application.

The O-oxyethyl-benzofurandione dioximes of the formula (XVI) are obtained when process r) O-oxyethyl-benzofurandione monooximes of the formula (XIV)

are reacted with hydroxylamine—or an acid addition complex thereof if appropriate in the presence of a diluent and, if appropriate, in the presence of an acid acceptor.

The O-oxyethyl-benzofurandione monooximes of the formula (XIV) required as starting materials in the practice of the process r) according to the invention have already been described in the description of the process n) according to the invention.

The O-oxyethyl-O'-methyl-benzofurandione dioximes of the formula (XIII) required as starting materials in the practice of the process m) according to the invention are defined in a general way by the formula (III). In this formula (XIII), A, $R^1$, $R^2$, $R^3$, $R^4$, $Z^1$, $Z^2$, $Z^3$ and $Z^4$ preferably or particularly have those meanings already mentioned in connection with the description of the compounds of the formula (I) which can be prepared according to the invention as being preferred or particularly preferred for A, $R^1$, $R^2$, $R^3$, $R^4$, $Z^1$, $Z^2$, $Z^3$ and $Z^4$. E represents an acyl group, preferably formyl, acetyl or benzoyl, or a ketal protecting group, preferably 2-tetrahydropyranyl, 1-methoxy-1-ethyl, 1-ethoxy-1-ethyl, methoxymethyl or ethoxymethyl.

The starting materials of the formula (XIII) have not been disclosed before, and as novel compounds they also form part of the subject matter of the present application.

The O-oxyethyl-O'-methyl-benzofurandione dioximes of the formula (XIII) are obtained when process s) O-oxyethyl-benzofurandione monooximes of the formula (XIV) are reacted with an alkoxyamine of the formula (IV)

or an acid addition complex thereof if appropriate in the presence of a diluent and, if appropriate, in the presence of an acid acceptor, or process t) O-oxyethyl-benzofurandione dioximes of the formula (XVI) are reacted with an alkylating agent of the formula (VI), if appropriate in the presence of a diluent and, if appropriate, in the presence of a base, or process u) O-alkyl-benzofurandione dioximes of the formula (VIII) are reacted with an ethanol derivative of the formula (XV), if appropriate in the presence of a diluent and, if appropriate, in the presence of an acid acceptor.

The O-oxyethyl-benzofurandione monooximes of the formula (XIV) required as starting materials in the practice of the process s) according to the invention have already been described in the description of the process n) according to the invention.

The O-oxyethyl-benzofurandione dioximes of the formula (XVI) required as starting materials in the practice of the process t) according to the invention have already been described in the description of the process q) according to the invention.

The O-alkyl-benzofurandione dioximes of the formula (VIII) required as starting materials in the practice of the process u) according to the invention have already been described in the description of the process e) according to the invention.

The hydroxybenzoyldioxazines required as starting materials in the practice of the process b) according to the invention are defined in a general way by the formula (III). In this formula (III), $R^1$, $R^2$, $R^3$, $R^4$, $Z^1$, $Z^2$, $Z^3$ and $Z^4$ preferably or particularly have those meanings already mentioned in connection with the description of the compounds of the formula (I) which can be prepared according to the invention as being preferred or particularly preferred for $R^1$, $R^2$, $R^3$, $R^4$, $Z^1$, $Z^2$, $Z^3$ and $Z^4$.

The starting materials of the formula (III) have not been disclosed before, and as novel compounds they also form part of the subject matter of the present application.

The hydroxybenzoyldioxazines of the formula (III) are obtained when process k) O-hydroxyethyl-benzofurandione monooximes of the formula (VII)

are reacted, if appropriate in the presence of a diluent and, if appropriate, in the presence of an acid or a base.

The O-hydroxyethyl-benzofurandione monooximes of the formula (VII) required as starting materials in the practice of the process k) according to the invention have already been described in the description of the process d) according to the invention.

The hydroxyphenyl-hydroximinomethyl-dioxazines required as starting materials in the practice of the process c) according to the invention are defined in a general way by the formula (V). In this formula (V), $R^1$, $R^2$, $R^3$, $Z^1$, $Z^2$, $Z^3$ and $Z^4$ preferably or particularly have those meanings already mentioned in connection with the description of the compounds of the formula (I) which can be prepared according to the invention as being preferred or particularly preferred for $R^1$, $R^2$, $R^3$, $R^4$, $Z^1$, $Z^2$, $Z^3$ and $Z^4$.

The starting materials of the formula (V) have not been disclosed before, and as novel compounds they also form part of the subject matter of the present application.

The hydroxyphenyl-hydroximinomethyl-dioxazines of the formula (V) are obtained when process l) hydroxybenzoyldioxazines of the formula (III) are reacted with hydroxylamine—or an acid addition complex thereof if appropriate in the presence of a diluent and, if appropriate, in the presence of an acid acceptor, or process v) O-hydroxyethyl-benzofurandione dioximes of the formula (X)

are rearranged, if appropriate in the presence of a diluent and, if appropriate, in the presence of an acid or a base.

The hydroxybenzoyldioxazines of the formula (III) required as starting materials in the practice of the process l) according to the invention have already been described in the description of the process b) according to the invention.

The O-hydroxyethyl-benzofurandione dioximes of the formula (X) required as starting materials in the practice of the process v) according to the invention have already been described in the description of the process f) according to the invention.

The alkoxyamines further required as starting materials in the practice of the processes b), d), h) and s) according to the invention are defined in a general way by the formula (IV). In this formula (IV), A preferably or particularly has that meaning already mentioned in connection with the description of the compounds of the formula (I) which can be prepared according to the invention as being preferred or particularly preferred for A. Preferred acid addition complexes of the alkoxyamines of the formula (IV) are their hydrochlorides, sulphates and hydrogen sulphates.

The alkoxyamines of the formula (IV) and their acid addition complexes are known chemicals for synthesis.

The alkylating agents further required as starting materials in the practice of the processes c), f), p) and t) according to the invention are defined in a general way by the formula (VI). In this formula (VI), A preferably or particularly has that meaning already mentioned in connection with the description of the compounds of the formula (I) which can be prepared according to the invention as being preferred or particularly preferred for A. X represents halogen, preferably chlorine, bromine or iodine, alkylsulphonyloxy, preferably methylsulphonyloxy, alkoxysulphonyloxy, preferably methoxysulphonyloxy, or arylsulphonyloxy, preferably 4-tolylsulphonyloxy.

The alkylating agents of the formula (VI) are known chemicals for synthesis.

The ethane derivatives further required as starting materials in the practice of the processes e) and g) according to the invention are defined in a general way by the formula (IX). In this formula (IX), $Z^1$, $Z^2$, $Z^3$ and $Z^4$ preferably or particularly have those meanings already mentioned in connection with the description of the compounds of the formula (I) which can be prepared according to the invention as being preferred or particularly preferred for $Z^1$, $Z^2$, $Z^3$ and $Z^4$. $Y^1$ represents halogen, preferably chlorine, bromine or iodine, alkylsulphonyloxy, preferably methylsulphonyloxy, arylsulphonyloxy, preferably 4-tolylsulphonyloxy, or alkanoyloxy, preferably acetyloxy. G represents hydrogen or is linked to $Y^1$ by a single bond, $Y^1$ being oxygen and G being carbonyl, or else G together with $Y^1$ represent a single bond.

The ethane derivatives of the formula (IX) are known chemicals for synthesis.

The hydroxylamine further required as starting material in the practice of the processes i), l) and r) according to the invention, or its acid addition complexes, preferably its hydrochloride, sulphate and hydrogen sulphate, are known chemicals for synthesis.

The ethanol derivatives further required as starting materials in the practice of the processes o) and u) according to the invention are defined in a general way by the formula (XV). In this formula (XV), $Z^1$, $Z^2$, $Z^3$ and $Z^4$ preferably or particularly have those meanings already mentioned in connection with the description of the compounds of the formula (I) which can be prepared according to the invention as being preferred or particularly preferred for $Z^1$, $Z^2$, $Z^3$ and $Z^4$. E preferably or particularly has that meaning already mentioned in connection with the description of the compounds of the formula (XIII) according to the invention as being preferred or particularly preferred for E. $Y^2$ represents halogen, preferably chlorine, bromine or iodine, alkylsulphonyloxy, preferably methylsulphonyloxy, arylsulphonyloxy, preferably 4-tolylsulphonyloxy, or alkanoyloxy, preferably acetyloxy.

The ethanol derivatives of the formula (XV) are known and can be prepared by known methods (cf. for example Newkome, George R.; Marston, Charles R., J. Org. Chem., 50, 22, 1985, 4238–4245; Henry, Chem. Ber., 7 <1874>, 70).

If the processes a), k) and v) according to the invention are carried out in the presence of an acid, suitable diluents are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, dioxane, 1,2-dimethoxyethane, 1,2-diethoxyethane or anisole; esters, such as methyl acetate or ethyl acetate, or sulphones, such as sulpholane, and also any mixtures of the diluents mentioned. Particularly preferred diluents are ethers, such as diethyl ether, 1,2-diethoxyethane or anisole; and aromatic hydrocarbons, such as, for example, benzene, toluene or xylene.

If the processes a), k) and v) according to the invention are carried in the presence of a base, suitable diluents are water and all organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and their mixtures with water. Preferred diluents are water, alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether; and their mixtures with water.

Particularly preferred diluents in this instance are water or alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and their mixtures with water.

Suitable diluents in the practice of the processes b), d), h), i), l), r) and s) according to the invention are all inert organic solvents. These preferably include aromatic hydrocarbons, such as, for example, benzene, toluene or xylene; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; amides, such as N,N-dimethylformamide, N,N-dimethylacetamide, N-methylformanilide, N-methylpyrrolidone or hexamethylphosphoric triamide; organic acids, such as acetic acid; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water. Particularly preferred diluents are amides, such as N,N-dimethylformamide, N,N-dimethylacetamide, N-methylformanilide, N-methylpyrrolidone or hexamethylphosphoric triamide; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, acids, such as acetic acid, their mixtures with water or pure water. Further particular preference is also given to two-phase mixtures, such as, for example, water/toluene.

Suitable diluents in the practice of the processes c), e), f), g), o), p), t) and u) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone, nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide, sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water. Particularly preferred diluents are ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether. Further particular preference is also given to two-phase mixtures, such as, for example, water/toluene.

Suitable diluents in the practice of the processes m), n) and q) according to the invention are water and all organic solvents. These preferably include ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide, esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The processes a), k) and v) according to the invention are, if appropriate, carried out in the presence of an acid or a base. Suitable acids include all inorganic or organic protic and Lewis acids, and also all polymeric acids. These include, for example, hydrogen chloride, hydrogen bromide, sulphuric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, zinc chloride, iron (III) chloride, antimony pentachloride, acid ion exchangers, acid clays and acid silica gel. Preference is given to hydrogen chloride or hydrogen bromide. Suitable bases include common inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potasium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU). Particularly preferred bases are sodium methoxide, sodium ethoxide, potassium tert-butoxide, sodium hydroxide, potassium hydroxide, ammonium hydroxide, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

If appropriate, the processes b), d), h), i), l), r) and s) according to the invention are carried out in the presence of a suitable acid acceptor. These include all common inorganic or organic bases. They preferably include alkaline earth metal or alkali metal hydroxides, alkoxides, acetates, carbonates or bicarbonates, such as, for example, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

If appropriate, the processes c), e), f), g), o), p), t) and u) are carried out in the presence of a suitable acid acceptor. These are all common inorganic or organic bases. These preferably include alkaline earth metal or alkali metal hydrides, hydroxides, amides, alkoxides, carbonates or bicarbonates, such as, for example, sodium hydride, sodium amide, sodium methoxide, sodium ethoxide, potassium tert-butoxide, sodium hydroxide, potassium hydroxide, sodium carbonate, potassium carbonate, potassium bicarbonate or sodium bicarbonate, and tertiary amines, such as trimethylamine, triethylamine, tributylamine, N,N-dimethylaniline,N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

In the practice of the processes a), k) and v) according to the invention, the reaction temperatures may be varied over a relatively wide range. The reactions are generally carried out at temperatures from –20° C. to 100° C., preferably at temperatures from –10° C. to 80° C.

In the practice of the processes b), d), h), i), l), r) and s) according to the invention, the reaction temperatures may be varied over a relatively wide range. The reactions are generally carried out at temperatures from 0° C. to 200° C., preferably at temperatures from 20° C. to 150° C.

In the practice of the processes c), e), f), g), o), p), t) and u) according to the invention, the reaction temperatures may be varied over a relatively wide range. The reactions are generally carried out at temperatures from –20° C. to 100° C., preferably at temperatures from 0° C. to 80° C.

The processes a) to v) according to the invention are generally carried out at atmospheric pressure. However, it is also possible to carry out the processes at elevated or reduced pressure—in general between 0.1 bar and 10 bar.

In a preferred process variant (A), a benzofurandione monooxime of the formula (XI) is initially converted into an O-hydroxyethyl-benzofurandione monooxime of the formula (VII) by reaction with an ethane derivative of the formula (IX), as described in process g). Without further purification, this is then reacted with an alkoxyamine of the formula (IV)—or an acid addition complex thereof—if appropriate in a buffer system such as, for example, sodium acetate/acetic acid as described in process d), to afford an O-hydroxyethyl-O'-methyl-benzofurandione dioxime of the formula (II) which, in turn, yields the desired 3-(1-hydroxyphenyl-1-alkoximinomethyl)dioxazine of the formula (I) without further purification on treatment with an acid or a base by the method of process a).

In a further preferred process variant (B), a benzofurandione monooxime of the formula (XI) is initially converted into an O-hydroxyethyl-benzofurandione monooxime of the formula (VII) by reaction with an ethane derivative of the formula (IX), as described in process g). Upon treatment with an acid or base, this affords a hydroxybenzoyldioxazine of the formula (III) which is then reacted with an alkoxyamine of the formula (IV)—or an acid addition complex thereof—to give the desired 3-(1-hydroxyphenyl-1-alkoximinomethyl)dioxazine of the formula (I).

In a third preferred process variant (C), a benzofurandione monooxime of the formula (XI) is initially converted into an O-alkyl-benzofurandione dioxime of the formula (VIII) by reaction with an alkoxyamine of the formula (IV)—or an acid addition complex thereof. This is then reacted with an ethane derivative of the formula (IX) to afford an O-hydroxyethyl-O'-methyl-benzofurandione dioxime of the formula (II) which on treatment with an acid or a base yields the desired 3-(1-hydroxyphenyl-1-alkoximinomethyl)dioxazine of the formula (I).

It is very surprising that the processes according to the invention, in particular when combined, yield high purity products in high yields. Chem. Ber. 1902, 1640, for example, describes that benzofurandione monooximes of the formula (XI) are cleaved to give salicylic acid derivatives or hydroxyphenylglyoxylic acid derivatives by treatment with acids and with bases. It was therefore unforeseeable that the 3-(1-hydroxyphenyl-1-alkoximinomethyl)dioxazines can be prepared without any significant side reactions in a reaction comprising only three steps.

The processes according to the invention have a number of advantages. They allow, for example, the preparation of a large quantity of 3-(1-hydroxyphenyl-1-alkoximinomethyl)dioxazines in high yields and high purities. It is a further advantage that the benzofurandione monooximes required as starting materials are obtainable in a simple manner even in major amounts (Beilstein, E (II) 17, 462; Mameli, G. 56, 768).

PROCESS AND PREPARATION EXAMPLES

Example 1

Process variant (A)

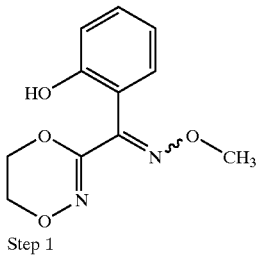

(1)

Step 1

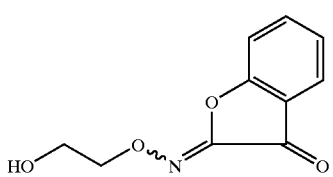

Compound (VII-1):

Process g)

11.8 g (0.0725 mol) of benzofuran-2,3-dione 2-oxime (XI-1) (Stoermer, Kahlert, B. 35, 1644) are dissolved in 75 ml of dimethylformamide. With cooling, 3 g (0.075 mol) of 60% strength sodium hydride (mineral oil suspension) are added a little at a time and stirring is continued at a temperature of 25° C. for about one hour until the formation of gas has ceased. The mixture is then cooled to 0° C., and at this temperature 9.3 g (0.0744 mol) of 2-bromoethanol are added dropwise and stirring is continued at 25° C. for a further 24 hours. The reaction mixture is poured into water and the resulting mixture is extracted with ethyl acetate, the organic phase is dried over sodium sulphate and the solvent is distilled off under reduced pressure. The residue is recrystallized from a mixture of 150 ml of toluene and 100 ml of cyclohexane. 11.5 g (64% of theory) of benzofuran-2,3-dione 2-[O-(2-hydroxy-ethyl)-oxime] (VII-1) are obtained (content according to HPLC analysis: 83.5%). A sample recrystallized from toluenes has a melting point of 110–111° C.

Step 2

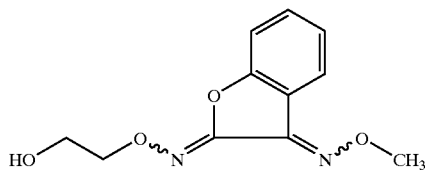

Compound (II-1):

Process d)

11.5 g of crude benzofuran-2,3-dione 2-[O-(2-hydroxy-ethyl)-oxime] (VII-1) and 5.15 g (0.0616 mol) of O-methylhydroxylamine hydrochloride are dissolved in 60 ml of dimethylformamide and stirred at 80° C. for 30 minutes. The reaction mixture is poured into water and the resulting mixture is extracted with ethyl acetate. The organic phase is dried over sodium sulphate and the solvent is distilled off under reduced pressure. 14.1 g of an oil containing 40.5% of benzofuran-2,3-dione 2-[O-(2-hydroxy-ethyl)-oxime] 3-(O-methyl-oxime) (II-1) and 14% of (5,6-dihydro-1,4,2-dioxazin-3-yl)-(2-hydroxyphenyl)-methanone O-methyl-oxime (1) are obtained.

Step 3

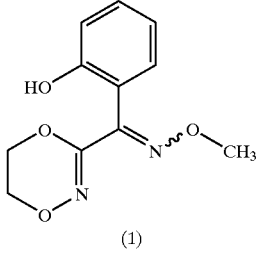

Compound (1):

(1)

Process a)

14.1 g of the oil from step 2 of the process A containing the compounds (II-1) and (1) are dissolved in 200 ml of diethyl ether which has been saturated beforehand with hydrogen chloride gas at 0° C. The mixture is stirred for 30 minutes without further cooling and then poured into a sodium bicarbonate solution cooled to 0° C. The organic phase is separated off and the aqueous phase is extracted repeatedly with diethyl ether. The combined organic phases are dried over sodium sulphate and concentrated at reduced pressure. The residue is stirred with tert-butyl methyl ether, whereupon the product crystallizes. 5.4 g (28% of theory based on benzofuran-2,3-dione 2-oxime) of crystalline (5,6-dihydro-1,4,2-dioxazin-3-yl)-(2-hydroxy-phenyl)-methanone O-methyl-oxime (1) are obtained (content according to HPLC analysis: 88.8%).

$^1$H NMR spectrum (CDCl$_3$/TMS): δ=4.10 (3H); 4.19/4.20/4.21/4.22 (2H); 4.47/4.48/4.49/4.50 (2H); 6.26 (1H); 6.95–7.0 (2H); 7.21/7.23 (1H); 7.31–7.36 (2H) ppm.

Example 2

Process variant B

Step 1

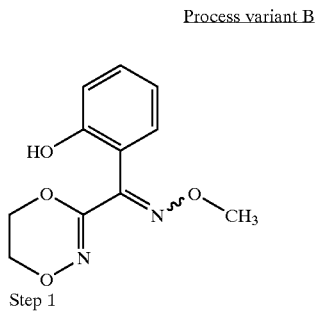
(1)

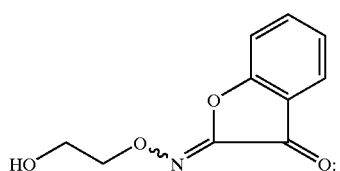
Compound (VII-1):

This step has already been described as process g) in step 1 of the process variant (A).

Step 2

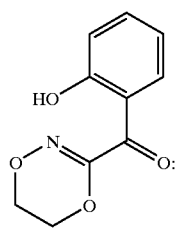
Compound (III-1):

Process k)

At 20° C., dry hydrogen chloride gas is passed through a mixture of 19 g (0.0917 mol) of benzofuran-2,3-dione 2-[O-(2-hydroxy-ethyl)-oxime] (VII-1) and 439 ml of diethyl ether, whereupon the mixture warms to 35° C. After 7 hours, the mixture is decanted from undissolved material and the solvent is distilled off under reduced pressure. The residue is taken up in ethyl acetate and washed first with 50 ml of water and then with 20 ml of a saturated aqueous sodium bicarbonate solution. The organic phase is separated off and dried over sodium sulphate and the solvent is distilled off under reduced pressure. 17 g of crude product are obtained. This product is chromatographed over silica gel using dichloromethane. 10 g (51.9% of theory based on the compound (VII-1)) of (5,6-dihydro-1,4,2-dioxazin-3-yl)-(2-hydroxy-phenyl)-methanone (III-1) of a purity of 98.7% (HPLC) are obtained.

$^1$H NMR (CDCl$_3$, TMS): δ=4.28/4.29/4.30/4.31 (2H); 4.55/4.56/4.57/4.58 (2H); 6.90/6.92/6.93/6.95/6.99 17.02 (2H); 7.50/7.51/7.53 17.54/7.55/7.56 (1H); 8.27/8.29/8.30 (1H); 11.52 (1H) ppm.

Step 3

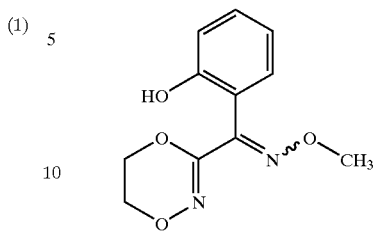
Compound (1):

Process b)

4.4 g (0.021 mol) of (5,6-dihydro-1,4,2-dioxazin-3-yl)-(2-hydroxy-phenyl)-methanone (III-1) and 1.87 g (0.022 mol) of O-methylhydroxylamine hydrochloride in 22 ml of dimethylformamide are heated to 100° C. for 2 hours. The reaction mixture is poured into water and the resulting mixture is extracted with ethyl acetate, the organic phase is dried over sodium sulphate and the solvent is distilled off under reduced pressure. 5.7 g of crude (5,6-dihydro-1,4,2-dioxazin-3-yl)-(2-hydroxy-phenyl)-methanone O-methyl-oxime (1) comprising 17.5% of the E isomer and 38% of the Z isomer by HPLC are obtained. This crude product is chromatographed over silica gel using a mixture of petroleum ether/tert-butyl methyl ether (1:1). 1.55 g of Z-(5,6-dihydro-1,4,2-dioxazin-3-yl)-(2-hydroxy-phenyl)-methanone O-methyl-oxime (I) of a purity of 91.5% (HPLC)=28.27% of theory) are obtained.

$^1$H NMR spectrum (CDCl$_3$/TMS): δ=4.08 (3H); 4.30/4.32/4.33 (2H); 4.53/4.54/4.55 (2H); 6.89 16.92/6.94 16.98/7.01 (2H); 7.28/7.31/7.33/7.34/7.35/7.37 (2H); 10.11 (1H) ppm.

Furthermore, 0.9 g of E-(5,6-dihydro-1,4,2-dioxazin-3-yl)-(2-hydroxy-phenyl)-methanone O-methyl-oxime (1) of a purity of 93.7% (HPLC) =16.8% of theory is obtained.

$^1$H NMR spectrum (CDCl$_3$/TMS): δ=4.09 (3H); 4.18/4.19/4.20/4.21 (2H); 4.47/4.48/4.50 (2H); 6.28 (1H: OH); 6.94/6.95/6.97 (2H); 7.20–7.36 (2H) ppm.

Example 3

Process variant C

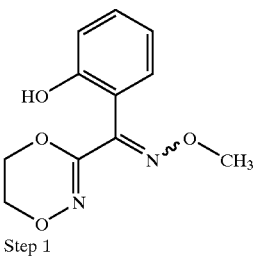
(1)

Step 1

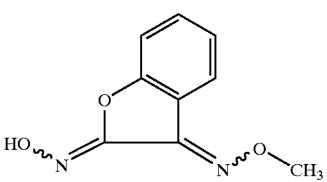
Compound (VIII-1):

Process h)

3.26 g (0.02 mol) of benzofuran-2,3-dione 2-oxime (XI-1) and 3.36 g (0.04 mol) of O-methylhydroxylamine hydrochloride in 20 ml of dimethylformamide are stirred for 20 minutes at 20° C. and then for 45 minutes at 80° C. The reaction mixture is poured into a mixture of aqueous sodium bicarbonate solution and ethyl acetate. The organic phase is separated off and dried over sodium sulphate and the solvent is distilled off under reduced pressure. The residue is stirred with diethyl ether. 1.4 g of crystalline benzofuran-2,3-dione 3-(O-methyl-oxime) 2-oxime (VIII-1) containing 70.7% of the stereoisomer A and 8.5% of the stereoisomer B by HPLC analysis are obtained.

$^1$H NMR spectrum (CDCl$_3$/TMS): δ=4.09 (3H, isomer B); 4.11 (3H, isomer A); 7.21–7.35 (2H); 7.51–7.65 (1H, isomer A and 2H, isomer B); 8.02/8.04/8.05 (1H, isomer A); 11.35 (1H, isomer A); 11.74 (1H, isomer B) ppm.

Step 2

Compound (II-1):

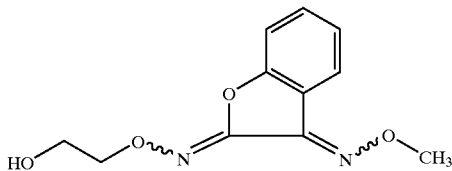

Process e)

4.49 g (0.0234 mol) of benzofuran-2,3-dione 3-(O-methyl-oxime) 2-oxime (VIII-1) are dissolved in 25 ml of dimethylformamide. 1 g (0.025 mol) of 60% strength sodium hydride is added to this solution which is then stirred at room temperature for one hour. 3.1 g (0.0248 mol) of 2-bromoethanol are added and the mixture is stirred at 25° C. for 12 hours. After the addition of 0.5 g of sodium methoxide and 1.22 g of 2-bromoethanol, the mixture is stirred at room temperature for 2 hours. A further 0.5 g of sodium methoxide and 1.22 g of 2-bromoethanol are added and the mixture is stirred for a further 2 hours at room temperature. The reaction mixture is poured into water and the resulting mixture is extracted with ethyl acetate and the organic phase is washed 3 times with 20 ml of 2 N aqueous sodium hydroxide solution. The solvent is distilled off under reduced pressure and the residue is chromatographed over silica gel using diethyl ether/petroleum ether (1:1). The eluent is distilled off under reduced pressure, affording 2.26 g (39.6% of theory) of benzofuran-2,3-dione 2-[O-(2-hydroxy-ethyl)-oxime] 3-(O-methyl-oxime) (II-1) which, according to HPLC, comprises 84.29% of stereoisomer A and 12.58% of stereoisomer B.

$^1$H NMR spectrum (CDCl$_3$/TMS): δ=3.95–4.03 (2H); 4.20 (3H, isomer B); 4.21 (3H, isomer A); 4.37–4.40 (2H); 7.14–7.21 (2H); 7.40–7.49 (1H), 7.6317.64/7.66 (1H, isomer B); 8.04/8.06/8.07 (1H, isomer A) ppm.

Step 3

Compound (1):

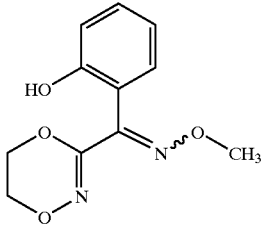

Process a)

2 g of benzofuran-2,3-dione 2-[O-(2-hydroxy-ethyl)-oxime] 3-(O-methyl-oxime) (II-1) (content according to HPLC analysis 96.88%, 0.0082 mol) prepared by the method of process e) are dissolved in 50 ml of diethyl ether saturated beforehand with hydrogen chloride gas at 0° C. Without further cooling, the mixture is stirred for 30 minutes, the solvent is then distilled off under reduced pressure and the residue is taken up once more in diethyl ether. Some of the product crystallizes out and is filtered off. The mother liquor is concentrated under reduced pressure and the residue is dissolved in 25 ml of diethyl ether saturated with hydrogen chloride gas at 0° C. Without further cooling, the solution is stirred for a further 30 minutes, the solvent is distilled off under reduced pressure and the residue is once more taken up in diethyl ether. A further fraction of the product crystallizes out and is likewise filtered off. In total, 1.37 g (69% of theory) of (5,6-dihydro-1,4,2-dioxazin-3-yl)-(2-hydroxy-phenyl)-methanone O-methyl-oxime (1) are obtained (content according to HPLC analysis: 97.59%).

$^1$H NMR spectrum (CDCl$_3$/TMS): δ=4.09 (3H): 4.18/4.19/4.20/4.21 (2H); 4.47/4.48/4.50 (2H); 6.94/6.95/6.97 (2H); 7.20–7.36 (2H) ppm.

Example 4

Process variant (D)

(I)

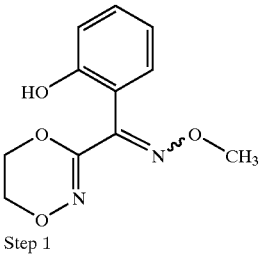

Step 1

Compound (XIV-1):

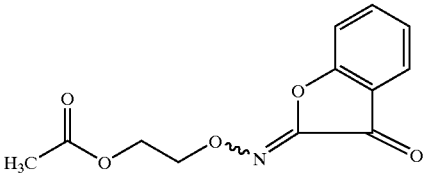

Process o)

1.63 g (0.01 mol) of benzofuran-2,3-dione 2-oxime (XI-1) in 5 ml of N-methyl-2-pyrrolidinone are stirred with 1.14 g (0.0108 mol) of sodium carbonate at 20° C. for 30 minutes. After the addition of 1.7 g (0.0102 mol) of 2-bromoethyl acetate, stirring is continued at 70° C. for 2 hours. The mixture is poured into 30 ml of water and the product is filtered off. The product is dried to afford 1.57 g (63% of theory) of crystalline 2-(3-oxo-3H-benzofuran-2-ylideneaminooxy)-ethyl acetate (XIV-1).

$^1$H NMR spectrum (CDCl$_3$/TMS): δ=2.11 (3H); 4.43/4.44/4.45/4.46/4.47 (2H); 4.52/4.54/4.55/4.57 (2H); 7.28/7.30/7.33 (2H); 7.72/7.74/7.76/7.78/7.80 (2H) ppm.

Step 2

Compound (XIII-1):

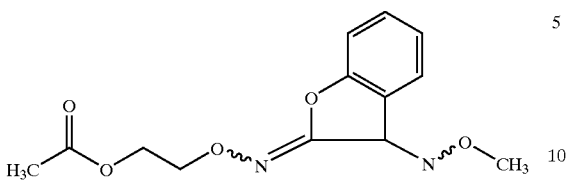

Process s)

10 g (0.04 mol) of 2-(3-oxo-3H-benzofuran-2-ylideneaminooxy)-ethyl acetate (XIV-1) and 4.18 g (0.05 mol) of O-methylhydroxylamine hydrochloride are dissolved in 40 ml of N-methyl-2-pyrrolidinone and stirred at 80° C. for 1 hour. The reaction mixture is poured into water and the resulting mixture is extracted with ethyl acetate. The organic phase is dried over sodium sulphate and the solvent is distilled off under reduced pressure. 10.6 g of crude product are obtained which are chromatographed over silica gel using tert-butyl methyl ether/petroleum ether (1:1). 6.9 g (59.1% of theory) of 2-(3-methoxyimino-3H-benzofuran-2-ylideneaminooxy)-ethyl acetate (XIII-1) having a content of 82.15% of isomer A and 13.38% of isomer B (HPLC) are obtained.

$^1$H NMR spectrum (CDCl$_3$/TMS): δ=2.10 (3H); 4.21 (3H, isomer B); 4.22 (3H, isomer A); 4.41–4.48 (4H); 7.15/7.17/7.20 (2H); 7.44–7.50 (1H); 7.63–7.66 (1H B); 8.05–8.09 (1H, isomer A) ppm.

Step 3

Compound (II-1):

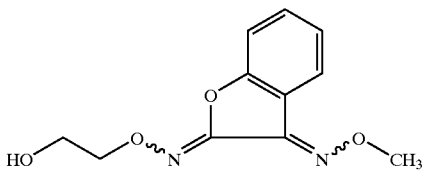

Process m)

2 g (0.00718 mol) of 2-(3-methoxyimino-3H-benzofuran-2-ylideneaminooxy)-ethyl acetate (XIII-1) in 8 ml of dimethylformamide are treated with 7.2 ml (0.0144 mol) of 2 N aqueous sodium hydroxide solution at 20° C. and stirred at 20° C. for 16 hours. The reaction mixture is poured into water and extracted with ethyl acetate. The organic phase is dried over sodium sulphate and the solvent is distilled off under reduced pressure. 1.7 g (67.6% of theory) of benzofuran-2,3-dione 2-[O-(2-hydroxy-ethyl)-oxime] 3-(O-methyl-oxime) (II-1) containing 56.8% of the stereoisomer A and 10.7% of the stereoisomer B by HPLC are obtained.

GC/MS analysis data (prior to analysis, the substance was silylated with N-methyl-N-trimethylsilyl trifluoroacetamide):

Stereoisomer A:
Retention index=2062
M$^+$=309, 308, 293, 249, 233, 192, 176, 145, 132, 89, 73, 45, 26.

Stereoisomer B:
Retention index=2000
M$^+$=309, 308, 293, 249, 218, 192, 176, 145, 132, 90, 73, 45.

Step 4

Compound (1):

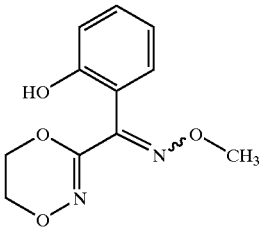

This step has already been described in step 3 of the process variant (A) and in step 3 of the process variant (C) as process a).

Further Examples of the Individual Processes

Example 5

Compound (1):

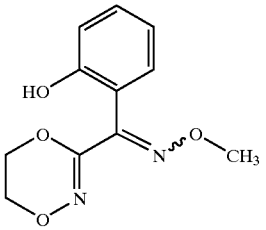

Process c)

1.2 g (0.0054 mol) of Z-(5,6-dihydro-1,4,2-dioxazin-3-yl)-(2-hydroxy-phenyl)-methanone oxime (V-1) in 5 ml of dimethylformamide are stirred at 20° C. together with 0.66 g (0.0062 mol) of sodium carbonate initially for 30 minutes. 0.83 g (0.00658 mol) of dimethyl sulphate is then added and stirring is continued at 20° C. for a further 16 hours. The reaction mixture is adjusted to a slightly acidic pH using 2 N aqueous hydrochloric acid and extracted with ethyl acetate. The organic phase is dried over sodium sulphate and the solvent is distilled off under reduced pressure. 0.8 g (50.35% of theory) of Z-(5,6-dihydro-1,4,2-dioxazin-3-yl)-(2-hydroxy-phenyl)-methanone O-methyl-oxime (1) of a purity of 80.3% (HPLC) is obtained.

$^1$H NMR spectrum (CDCl$_3$/TMS): δ=4.08 (3H); 4.30/4.32/4.33 (2H); 4.53/4.54/4.55 (2H); 6.89/6.92/6.98/7.01 (2H); 7.28/7.31/7.33/7.34/7.35/7.37 (2H); 10.11 (1H) ppm.

Example 6

Compound (II-1):

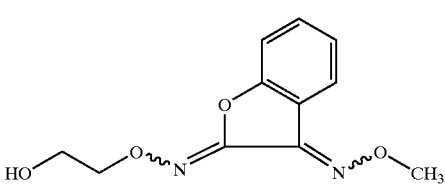

Process e)

3.19 g (0.0166 mol.) of benzofuran-2,3-dione 3-(O-methyl-oxime) 2-oxime (VIII-1) (mixture of 2 stereoisomers A:B=13:86) are suspended in 20 ml of methanol and treated dropwise with 8.3 g of a 2 molar sodium methoxide solution at 20° C. After the mixture has turned homogeneous, the methanol is distilled off under reduced pressure and the crystalline residue is dried in a desiccator for 12 hours. 3.55 g of the sodium salt of benzofuran-2,3-dione 3-(O-methyl-oxime) 2-oxime (VIII-1) are obtained. This salt is suspended in 16 ml of N-methyl-2-pyrrolidinone at 20° C., and 2.1 g (0.0168 mol) of 2-bromoethanol are added. The mixture is stirred at 20° C. for 48 hours. The reaction mixture is poured into water and the resulting mixture is extracted with ethyl acetate, and the organic phase is washed 3 times with 20 ml of 2 N aqueous sodium hydroxide solution. The solvent is distilled off under reduced pressure and the residue is chromatographed over silica gel using diethyl ether/petroleum ether (1:1). The eluent is distilled off under reduced pressure, affording 2.91 g (73.8% of theory) of benzofuran-2,3-dione 2-[O-(2-hydroxy-ethyl)-oxime] 3-(O-methyl-oxime) (II-1) consisting of 88.6% of stereoisomer B, 7.7% of stereoisomer A and 3.2% of stereoisomer C(HPLC).

$^1$H NMR spectrum (CDCl$_3$/TMS): δ=3.43 (1H, broad); 4.0–4.03 (2H); 4.20 (3H); 4.38–4.41 (2H); 7.14–7.21 (2H); 7.40/7.42/7.43/7.445 (1H); 7.63/7.67/7.66 (1H) ppm.

Example 7

Compound (II-1):

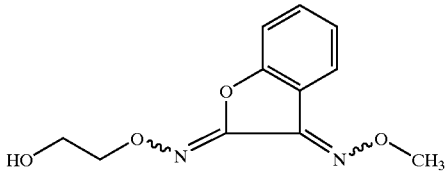

Process f)

At 20° C., 0.44 g (0.002 mol) of benzofuran-2,3-dione 2-[O-(2-hydroxy-ethyl)-oxime] 3-oxime α-1) in 5 ml of dimethylformamide are stirred with 0.08 g (0.002 mol) of 60% strength sodium hydride for 20 minutes. After the formation of gas has ended, 0.28 g (0.002 mol) of methyl iodide is added and the mixture is stirred at 20° C. for 16 hours. The reaction mixture is poured into water and the resulting mixture is extracted with ethyl acetate, the organic phase is dried over sodium sulphate and the solvent is distilled off under reduced pressure to afford 0.5 g (35% of theory) of crude product. According to HPLC analysis, the crude product contains 23% of the stereoisomer A and 10.1% of the stereoisomer B of benzofuran-2,3-dione 2-[O-(2-hydroxy-ethyl)-oxime] 3-(O-methyl-oxime) (II-1).

GC/MS analysis data (prior to analysis, the substance was silylated with N-methyl-N-trimethylsilyltrifluoroacetamide):

Retention index=2053 (isomer A)

M$^+$=309, 308, 293, 249, 233, 192, 176, 145, 132, 89, 73, 45, 26.

Retention index=1997 (isomer B)

M$^+$=309, 308, 293, 249, 218, 192, 176, 145, 132, 90, 73, 45.

Additionally, the crude product contains 20.5% (HPLC) of N-[2-(2-hydroxy-ethoxyimino)-benzofuran-3-ylidene]-N-methylamine N-oxide.

GC/MS analysis (silylated sample):

Retention index=2234

M$^+$=310, 308, 233, 192, 175, 159, 132, 102, 73, 45, 26).

Example 8

Compound (X-1):

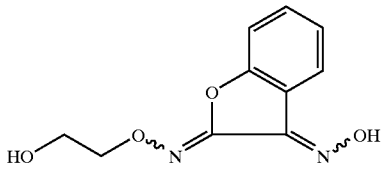

Process i)

At 80° C., 10.1 g (0.05 mol) of benzofuran-2,3-dione 2-[O-(2-hydroxy-ethyl)-oxime] (VII-1) in 50 ml of N-methyl-2-pyrrolidinone are stirred with 3.5 g of hydroxy-lamine hydrochloride for 2 hours. The reaction mixture is poured into water and the resulting mixture is extracted with ethyl acetate, the organic phase is dried over sodium sulphate and the solvent is distilled off under reduced pressure. The residue is then chromatographed over silica gel using tert-butyl methyl ether/petroleum ether (1:1). The eluent is distilled off under reduced pressure, affording 4.2 g (29.6% of theory) of benzofuran-2,3-dione 2-[O-(2-hydroxy-ethyl)-oxime] 3-oxime consisting of 62.4% of isomer A and 15.8% of isomer B (HPLC).

$^1$H NMR spectrum (DMSO-d$_6$/TMS): δ=3.64–3.71 (2H); 4.10–4.26 (2H); 4.78–4.87 (1H); 7.2–7.3 (1H); 7.3–7.4 (1H); 7.5–7.7 (1H); 8.11–8.14 (1H); 12.82 (1H, isomer A); 12.91 (1H, isomer B) ppm.

Example 9

Compound (V-1):

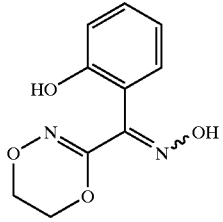

Process l)

At 80° C., 4.14 g (0.02 mol) of (5,6-dihydro-1,4,2-dioxazin-3-yl)-(2-hydroxy-phenyl)-methanone (III-1) in 20 ml of dimethylformamide are stirred with 2.1 g (0.03 mol) of hydroxylamine hydrochloride for 2 hours. The reaction mixture is poured into water and the resulting mixture is extracted with ethyl acetate, and the organic phase is dried over sodium sulphate and concentrated under reduced pressure. 4.7 g of crude product consisting of 15% E isomer and 57.5% Z isomer (HPLC) are obtained. The crude product is chromatographed over silica gel using a mixture of diethyl ether and petroleum ether (1:1). 2.7 g (60.8% of theory) of (5,6-dihydro-1,4;2-dioxazin-3-yl)-(2-hydroxy-phenyl)-methanone oxime (V-1) are obtained (content according to HPLC analysis: 93.4%).

$^1$H NMR spectrum (DMSO-d$_6$/TMS): δ=4.19/4.20/4.21 (2H); 4.45/4.46/4.47 (2H); 6.89–6.92 (2H); 7.22–7.32 (1H); 7.33–7.40 (1H); 10.30 (1H); 12.16 (1H) ppm.

Example 10

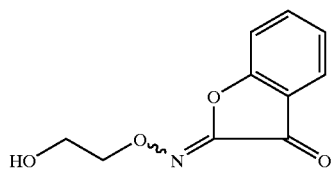

Compound (VII-1):

Process n)

2.07 g (0.01 mol) of benzofuran-2,3-dione 2-{O-[2-(tetrahydropyran-2-yloxy)-ethyl]-oxime} (XIV-2) are dissolved in 12 ml of methanol and stirred at room temperature with 100 mg of acidic ion exchanger resin for 16 hours. 40 ml of methanol are added to the reaction mixture which is then warmed until the crystals have dissolved. The acidic ion exchanger resin is filtered off, the filtrate is concentrated and the residue is recrystallized from 10 ml of toluene. 1.69 g (81.5% of theory) of crystalline benzofuran-2,3-dione 2-[O-(2-hydroxy-ethyl)-oxime] (VII-1) of melting point 110–111° C. are obtained.

$^1$H NMR spectrum (CDCl$_3$/TMS): δ=2.33 (1H, broad), 4.00–4.03 (2H); 4.47–4.50 (2H); 7.27–7.32 (2H); 7.70–7.78 (2H) ppm.

Example 11

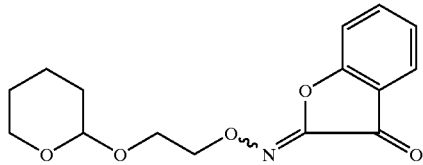

Compound (XIV-2):

Process o)

5 g (0.03 mol) of benzofuran-2,3-dione 2-oxime (XI-1) are dissolved in 30 ml of methanol, and at 20° C. 15 ml of a 2 molar solution of sodium methoxide in methanol are added dropwise. The solvent is distilled off under reduced pressure. The crystalline residue is dissolved in 30 ml of N-methyl-2-pyrrolidinone and treated with 6.27 g (0.03 mol) of 2-(2-bromoethoxy)-tetrahydropyran at 20° C. The reaction mixture is stirred for 16 hours at 20° C., poured into 100 ml of water and the resulting mixture is extracted twice with 100 ml of dichloromethane each time. The solvent is distilled off under reduced pressure and the residue is chromatographed over silica gel using a mixture of diethyl ether/dichloromethane/petroleum ether (1:1:2). 5.55 g (62.1% of theory) of benzofuran-2,3-dione 2-{O-[2-(tetrahydropyran-2-yloxy)-ethyl]-oxime} (XIV-2) are obtained.

$^1$H NMR spectrum (CDCl$_3$/TMS): δ=1.50–1.86 (6H); 3.49–3.53 (1H); 3.81–3.88 (2H); 4.02–4.09 (1H); 4.52–4.55 (2H); 4.66–4.69 (1H); 7.26–7.31 (2H); 7.69–7.80 (2H) ppm.

Example 12

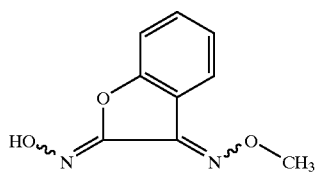

Compound (VIII-1):

Process p)

A solution of 11 g (0.0617 mol) of benzofuran-2,3-dione dioxime in 50 ml of dimethylformamide is added dropwise to a suspension of 2.4 g (0.06 mol) of 60% strength sodium hydride in 25 ml of dimethylformamide, and stirring is effected at 20° C. for one hour. 7.55 g (0.06 mol) of dimethyl sulphate are then added dropwise and stirring is continued at 20° C. for a further 16 hours. The reaction mixture is poured into water and the resulting mixture is extracted with ethyl acetate, the organic phase is dried over sodium sulphate and concentrated under reduced pressure. The residue is chromatographed over silica gel using hexane/acetone (7:3). Stirring the residue with diethyl ether affords 0.7 g of benzofuran-2,3-dione 3-(O-methyl-oxime) 2-oxime (VIII-1) as a mixture of stereoisomers consisting of 90.6% of isomer A and 9% of isomer B (HPLC).

Example 13

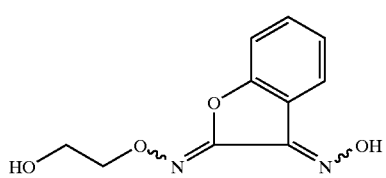

Compound (X-1):

Process q)

At 20° C., 5.28 g (0.02 mol) of 2-(3-hydroxyimino-3H-benzofuran-2-ylideneaminooxy)-ethyl acetate (XVI-1) in 20 ml of dimethylformamide are stirred with 4.24 g (0.048 mol) of 45% strength aqueous sodium hydroxide solution for 3 hours. The mixture is acidified with 2 N hydrochloric acid and extracted with ethyl acetate, the organic phase is dried over sodium sulphate and the solvent is distilled off under reduced pressure. According to HPLC analysis, the crude product contains 23.4% of the stereoisomer A and 4.1% of the stereoisomer B of benzofuran-2,3-dione 2-[O-(2-hydroxy-ethyl)-oxime] 3-oxime (X-1). Stirring the crude product with diethyl ether affords 1.4 g (28.5% of theory) of crystalline benzofuran-2,3-dione 2-[O-(2-hydroxy-ethyl)-oxime] 3-oxime α-1) consisting of 84.7% of stereoisomer A and 6% of stereoisomer B (HPLC).

$^1$H NMR spectrum (DMSO-d$_6$/TMS): δ=3.64–3.71 (2H); 4.10–4.26 (2H); 4.78–4.87 (1H); 7.2–7.3 (1H); 7.3–7.4 (1H); 7.5–7.7 (1H); 8.11–8.14 (1H); 12.82 (1H, stereoisomer A); 12.91 (1H, stereoisomer B) ppm.

Example 14

Compound (XVI-1):

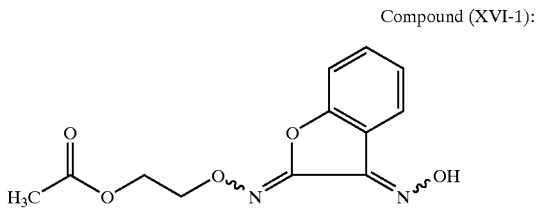

Process r)

5 g (0.02 mol) of 2-(3-oxo-3H-benzofuran-2-ylideneaminooxy)-ethyl acetate (XIV-1) and 1.74 g (0.025 mol) of hydroxylamine hydrochloride are dissolved in 20 ml of dimethylformamide and stirred at 100° C. for 2 hours. The reaction mixture is poured into water and the resulting mixture is extracted with ethyl acetate. The organic phase is dried over sodium sulphate and the solvent is dissolved off under reduced pressure. The residue is chromatographed over silica gel using tert-butyl methyl ether/petroleum ether (1:1). 2.7 g (38.5% of theory) of 2-(3-hydroxyimino-3H-benzofuran-2-ylideneaminooxy)-ethyl acetate (XVI-1) consisting of 64.23% of stereoisomer A and 14.9% of stereoisomer B (HPLC) are obtained.

$^1$H NMR spectrum (CDCL$_3$-d$_6$/TMS): δ=2.11 (3H, stereoisomer A); 2.12 (3H, stereoisomer B); 4.43–4.46 (4H); 7.19–7.23 (2H); 7.46–7.52 (1H); 7.65–7.8 (1H, stereoisomer B); 8.16/8.17/8.19 (1H, stereoisomer A); 8.9 (1H) ppm.

Example 15

Compound (XIII-1):

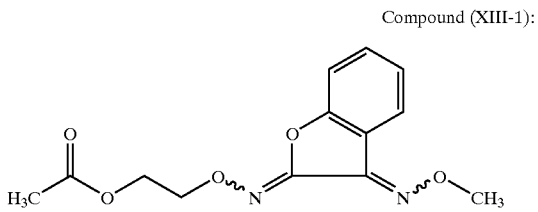

Process s)

10 g (0.04 mol) of 2-(3-oxo-3H-benzofuran-2-ylideneaminooxy)-ethyl acetate (XIV-1) and 4.18 g (0.05 mol) of O-methylhydroxylamine hydrochloride are dissolved in 40 ml of N-methyl-2-pyrrolidinone and stirred at 80° C. for 1 hour. The reaction mixture is poured into water and the resulting mixture is extracted with ethyl acetate. The organic phase is dried over sodium sulphate and the solvent is distilled off under reduced pressure. 10.6 g of crude 2-(3-methoxyimino-3H-benzofuran-2-ylideneaminooxy)-ethyl acetate (XIII-1) are obtained, which are chromatographed over silica gel using a mixture of tert-butyl methyl ether and petroleum ether (1:1). 6.9 g (59.1% of theory) of 2-(3-methoxyimino-3H-benzofuran-2-ylideneaminooxy) ethyl acetate (XIII-1) having a content of 82.15% of stereoisomer A and 13.38% of stereoisomer B are obtained.

$^1$H NMR spectrum (CDCl$_3$/TMS): δ=2.10 (3H); 4.21 (3H, stereoisomer B); 4.22 (3H, stereoisomer A); 4.41–4.48 (4H); 7.15/7.17/7.20 (2H); 7.44–7.50 (1H); 8.05–8.09 (1H) ppm.

Example 16

Compound (XIII-1):

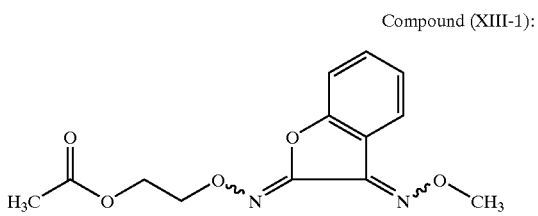

Process t)

0.26 g (0.001 mol) of 2-(3-hydroxyimino-3H-benzofuran-2-ylideneaminooxy)-ethyl acetate (XVI-1) is dissolved in 2 ml of dimethylformamide. At 20° C., 0.04 g (0.001 mol) of 60% strength sodium hydride is added and the mixture is stirred until the formation of gas has ended. 0.05 g (0.0005 mol) of sodium carbonate and 0.13 g (0.001 mol) of dimethyl sulphate are then added to the reaction mixture which is then left standing at 20° C. for 2 days. The reaction mixture is poured into water and the resulting mixture is extracted with ethyl acetate. The organic phase is dried over sodium sulphate and the solvent is distilled off under reduced pressure. 0.24 g (42.5% of theory) of crude 2-(3-methoxyimino-3H-benzofuran-2-ylideneaminooxy)-ethyl acetate (XIII-1) containing 33.9% of stereoisomer A and 15.4% of stereoisomer B according to HPLC analysis is obtained.

GC/MS analysis data:
Retention index=2097 (stereoisomer A)
M$^+$=279, 278, 218, 187, 160, 144, 130, 87, 75, 43, 26.
Retention index=2036 (stereoisomer B)
M$^+$=279, 278, 218, 187, 160, 144, 130, 87, 63, 43, 26.

Example 17

Compound (XIII-1):

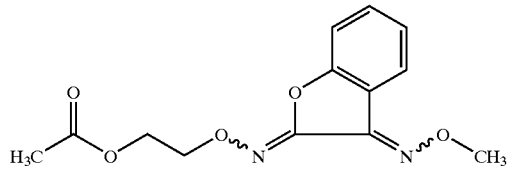

Process u)

At 20° C., 1.92 g (0.01 mol) of benzofuran-2,3-dione 3-(O-methyl-oxime) 2-oxime (VIII-1) are dissolved in 10 ml of dimethylformamide. 0.4 g (0.01 mol) of 60% strength sodium hydride is added to this solution and the mixture is stirred at 20° C. for 1 hour. 1.67 g (0.01 mol) of 2-bromoethyl acetate are then added, and stirring at 20° C. is continued for 16 hours. The reaction mixture is poured into water and the resulting mixture is extracted with ethyl acetate. The organic phase is dried over sodium sulphate and concentrated under reduced pressure. 2.3 g (52.6% of theory) of 2-(3-methoxyimino-3H-benzofuran-2-ylideneaminooxy)-ethyl acetate (XIII-1) consisting of 51.17% of stereoisomer A and 12.49% of stereoisomer B (HPLC) are obtained.

GC/MS analysis data (prior to analysis, the substance was silylated with N-methyl-N-trimethylsilyltrifluoroacetamide):
Retention index=2097 (stereoisomer A)
M$^+$=279, 278, 218, 187, 160, 144, 130, 87, 75, 43, 26.
Retention index=2035 (stereoisomer B)
M$^+$=279, 278, 218, 187, 160, 144, 130, 87, 75, 43, 26.

Example 18

Compound (V-1):

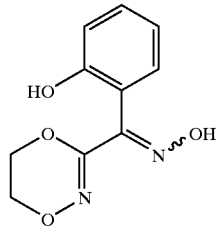

Process v)

1.11 g (0.005 mol) of benzofuran-2,3-dione 2-[O-(2-hydroxy-ethyl)-oxime] 3-oxime (X-1) are dissolved in 20 ml of diethyl ether which has been saturated beforehand with hydrogen chloride gas at 0° C. Without further cooling, the mixture is stirred for 3 hours and then poured into a sodium bicarbonate solution cooled to 0° C. The organic phase is separated off and the aqueous phase is extracted repeatedly with ethyl acetate. The combined organic phases are dried over sodium sulphate and concentrated under reduced pressure. 0.8 g (29.9% of theory) of crude (5,6-dihydro-1,4,2-dioxazin-3-yl)-(2-hydroxy-phenyl)-methanone oxime (V-1) consisting of 19.7% E isomer and 21.8% Z isomer (HPLC) is obtained.

GC/MS analysis data (prior to analysis, the substance was silylated with N-methyl-N-trimethylsilyltrifluoroacetamide):

Retention index=1980 (E isomer)
$M^+$=368, 351, 307, 292, 250, 235, 203, 176, 147, 117, 100, 73, 45.

Retention index=2036 (Z isomer)
$M^+$=367, 351, 306, 292, 250, 235, 203, 176, 147, 117, 100, 73, 45.

Annex: Reaction scheme

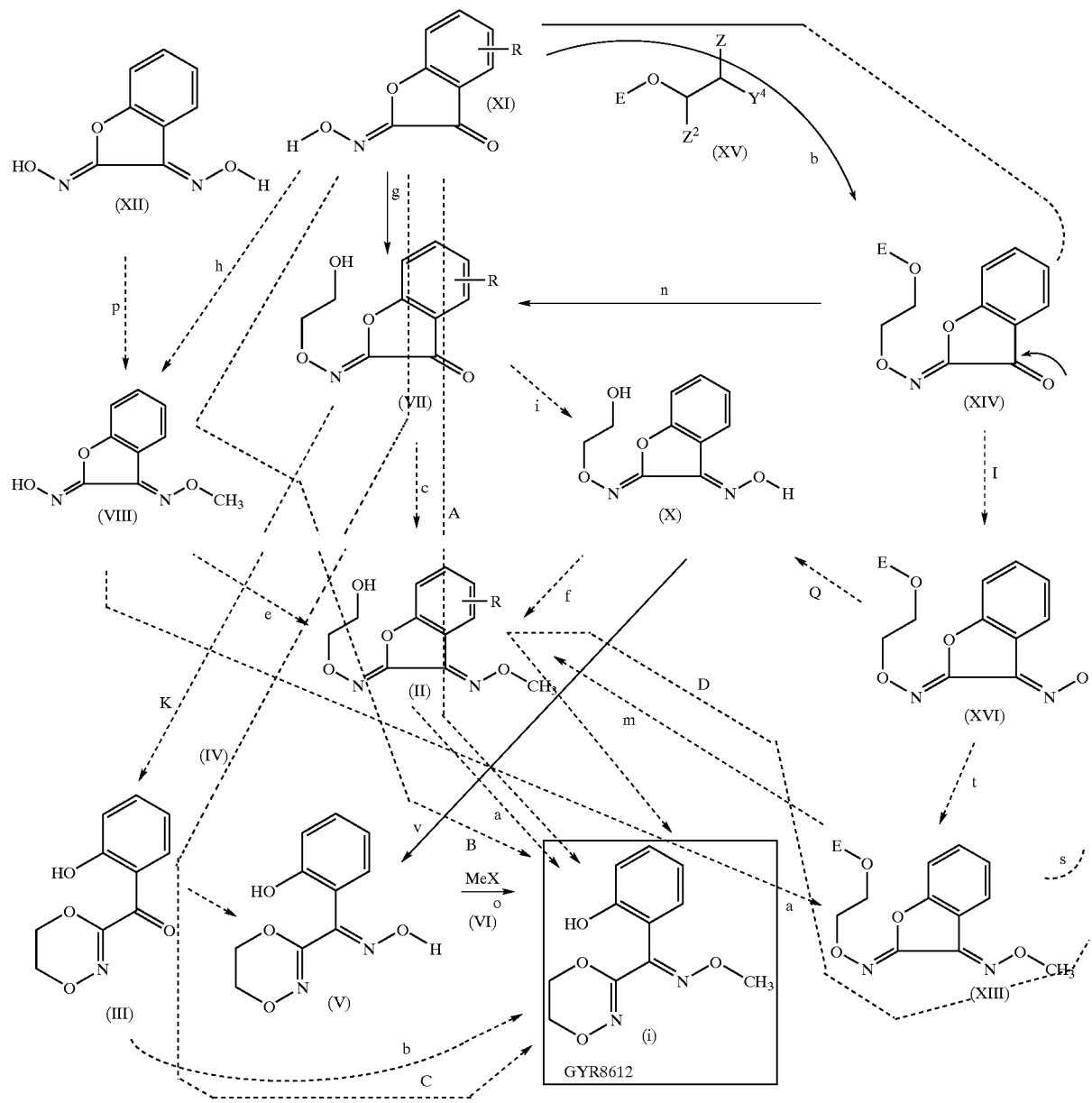

Hierarchy of the process steps

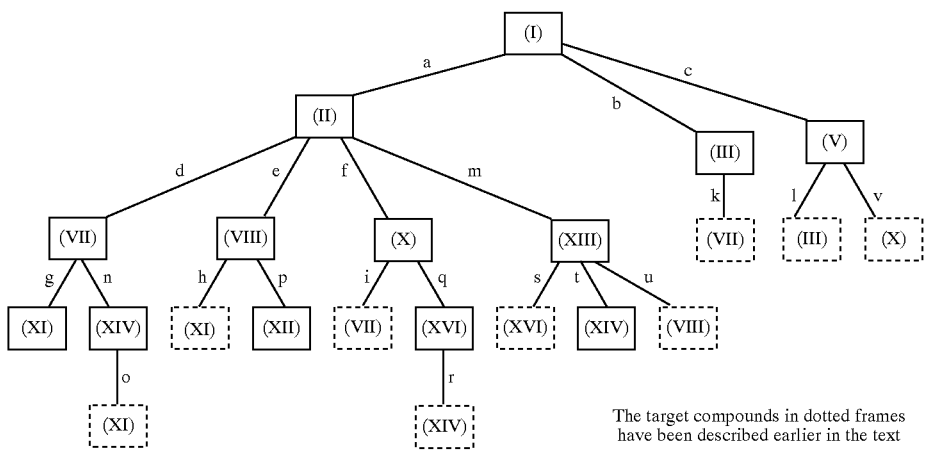

The target compounds in dotted frames have been described earlier in the text

What is claimed is:

1. Process for preparing compounds of the formula (I):

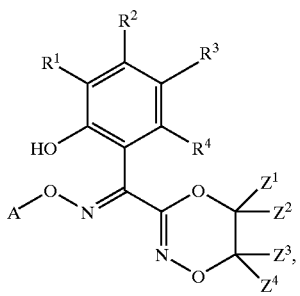

(I)

in which
  A represents alkyl,
  $R^1$, $R^2$, $R^3$ and $R^4$ are identical or different and each represent independently of one another hydrogen, halogen, cyano, nitro, respectively optionally substituted halogen-substituted alkyl, alkoxy, alkylthio, alkylsulphinyl or alkylsulphonyl, and
  $Z^1$, $Z^2$, $Z^3$ and $Z^4$ are identical or different and each represent independently of one another hydrogen, alkyl, halogenoalkyl or hydroxyalkyl, or
  $Z^1$ and $Z^2$ or $Z^1$ and $Z^3$ or $Z^3$ and $Z^4$ form together with the respective carbon atoms that they are attached to a cycloaliphatic ring,
characterized in that
  b) hydroxybenzoyldioxazines of the formula

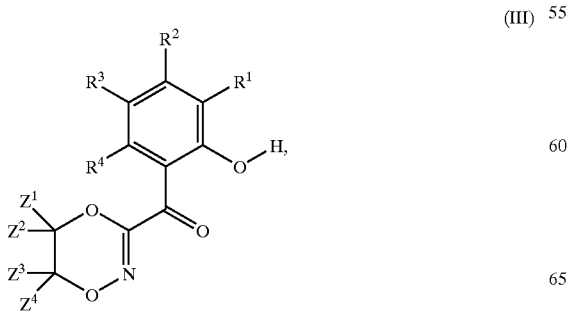

(III)

in which
  $R^1$, $R^2$, $R^3$, $R^4$, $Z^1$, $Z^2$, $Z^3$ and $Z^4$ are each as defined above,
are reacted with an alkoxyamine of the formula

A—O—NH$^2$ (IV)

in which
  A is as defined above
  —or an acid addition complex thereof—
  if appropriate in the presence of a diluant and, if appropriate, in the presence of an acid acceptor, or c) hydroxyphenyl-hydroximinomethyl-dioxazines of the formula

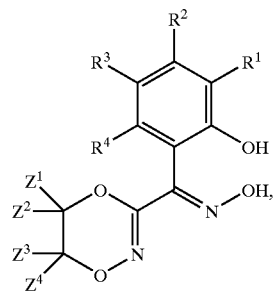

(V)

in which
  $R^1$, $R^2$, $R^3$, $R^4$, $Z^1$, $Z^2$, $Z^3$ and $Z^4$ are each as defined above,
are reacted with an alkylating agent of the formula

A—X (VI)

in which
  A is as defined above, and
  X represents halogen, alkylsulphanyloxy, alkoxysulphonyloxy or arylsulphonyloxy, if appropriate in the presence of a diluent and, if appropriate, in the presence of a base.

2. Compounds of the formula (III)

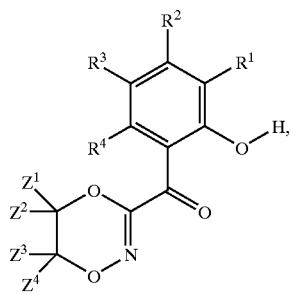
(III)

in which
R$^1$, R$^2$, R$^3$, R$^4$ are identical or different and each represent independently of one another hydrogen, halogen, cyano, nitro, respectively optionally halogen-substituted alkyl, alkoxy, alkylthio, alkylsulphiny or alkylsulphonyl, and Z$^1$, Z$^2$, Z$^3$ and Z$^4$ are identical or different and each represent independently of one another hydrogen, alkyl, halogenoalkyl or hydroxyalkyl, or Z$^1$ and Z$^2$ or Z$^1$ and Z$^3$ or Z$^3$ and Z$_4$ form together with the respective carbon atoms that they are attached to a cycloaliphatic ring.

3. Process for preparing compounds of the formula (III) as defined in claim 18, wherein k) O-hydroxyethyl-benzofurandione monooximes of the formula (VII):

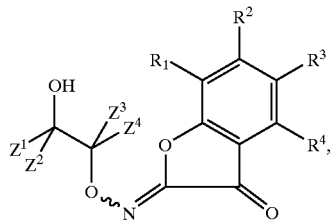
(VII)

wherein R$^1$–R$^4$ and Z$^1$–Z$^4$ are as defined in claim 2, are reacted, if appropriate in the presence of a diluent and, if appropriate, in the presence of an acid.

4. Compounds of the formula (V)

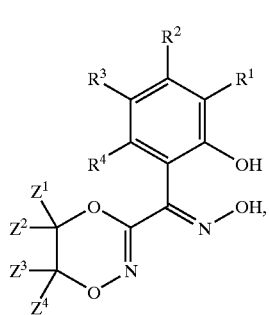
(V)

in which
R$^1$, R$^2$, R$^3$, R$^4$ are identical or different and each represent independently of one another hydrogen, halogen, cyano, nitro, respectively optionally halogen-substituted alkyl, alkoxy, alkylthio, alkylsulphiny or alkylsulphonyl, and Z$^1$, Z$^2$, Z$^3$ and Z$^1$ are identical or different and each represent independently of one another hydrogen, alkyl, halogenoalkyl or hydroxyalkyl, or Z$^1$ and Z$^2$ or Z$^1$ and Z$^3$ or Z$^3$ and Z$^4$ form together with the respective carbon atoms that they are attached to a cycloaliphatic ring.

5. Process for preparing compounds of the formula (V) as defined in claim 4, wherein l) hydroxybenzoyldioxazines of the formula (III):

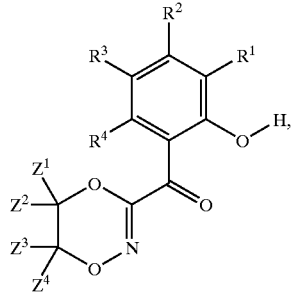
(III)

wherein R$^1$–R$^4$ and Z$^1$–Z$^4$ are as defined in claim 4, are reacted with hydrorylamine—or an acid addition complex thereof—if appropriate in the presence of a diluent and, if appropriate, in the presence of an acid acceptor, or r) O-hydroxyethyl-benzofurandione dioximes of the formula (X):

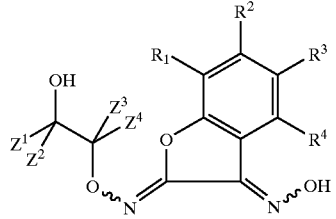
(X)

wherein R$^1$–R$^4$ and Z$^1$–Z$^4$ are as defined in claim 4, are rearranged, if appropriate in the presence of a diluent and, if appropriate, in the presence of an acid.

6. A compound of the formula:

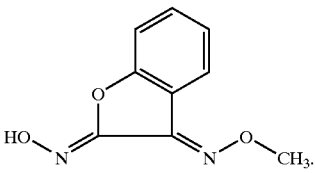

* * * * *

UNITED STATES PATENT AND TRADEMARK OFFICE
CERTIFICATE OF CORRECTION

PATENT NO. : 6,730,799 B2
DATED : May 4, 2004
INVENTOR(S) : Gayer et al.

It is certified that error appears in the above-identified patent and that said Letters Patent is hereby corrected as shown below:

Column 3,
Line 47, "A R$^1$,R$^2$," should read -- A, R$^1$, R$^2$, --

Column 4,
Line 56, "1 to halogen atoms" should read -- 1 to 5 halogen atoms --

Column 28,
Line 61, "3-oxime α1)" should read -- 3-oxime(X-1) --

Column 35,
Line 27, "Z$_4$" should read -- Z$^4$ --
Line 30, "defined in claim 18" should read -- defined in claim 2 --

Signed and Sealed this

Twenty-first Day of September, 2004

JON W. DUDAS
*Director of the United States Patent and Trademark Office*